United States Patent
Mathias et al.

(10) Patent No.: US 6,997,893 B2
(45) Date of Patent: Feb. 14, 2006

(54) CONFINED AIR TUBE AND METHODS FOR HANDLING AIR IN CLOSED BLOOD PROCESSING SYSTEMS

(75) Inventors: Jean-Marie Mathias, Lillois (BE); Jean-Marc Payrat, Nivelles (BE); Thomas Coneys, Feusines (FR); Philippe Van Heems, La Chatre (FR)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/619,870

(22) Filed: Jul. 15, 2003

(65) Prior Publication Data

US 2004/0015147 A1    Jan. 22, 2004

Related U.S. Application Data

(63) Continuation of application No. 09/902,313, filed on Jul. 10, 2001, now abandoned, which is a continuation of application No. 09/082,946, filed on May 21, 1998, now Pat. No. 6,267,745.

(51) Int. Cl.
  *A61M 37/00* (2006.01)
  *A61M 5/00* (2006.01)
  *A61B 19/00* (2006.01)

(52) U.S. Cl. .................... 604/6.15; 604/4.01; 604/408; 604/411

(58) Field of Classification Search .............. 604/4.01, 604/5.01, 6.09, 6.15–6.16, 7, 264, 403, 406, 604/408–416; 128/DIG. 24; 422/99, 101, 422/26; 206/828; 220/62.11, 62.22; 383/33, 383/37, 127
See application file for complete search history.

(56) References Cited

U.S. PATENT DOCUMENTS

| | | | |
|---|---|---|---|
| 3,058,799 A | 10/1962 | Rowles, Jr. | |
| 4,786,286 A | 11/1988 | Cerny et al. | |
| 4,790,815 A * | 12/1988 | Balteau et al. | ................. 604/29 |
| 5,128,048 A | 7/1992 | Stewart et al. | |
| 5,167,656 A | 12/1992 | Lynn | |
| 5,269,946 A | 12/1993 | Goldhaber et al. | |
| 5,283,033 A | 2/1994 | Dodrill | |
| 5,445,629 A | 8/1995 | Debrauwere et al. | |
| 5,451,321 A | 9/1995 | Matkovich | |
| 5,472,621 A | 12/1995 | Matkovich | |
| 5,514,106 A | 5/1996 | D'Silva | |
| 5,601,730 A * | 2/1997 | Page et al. | .................. 210/806 |
| 5,695,489 A | 12/1997 | Japuntich | |
| 5,928,214 A | 7/1999 | Rubinstein et al. | |
| 5,941,866 A | 8/1999 | Niedospial, Jr. | |
| 6,267,745 B1 * | 7/2001 | Mathias et al. | ............. 604/4.01 |

* cited by examiner

Primary Examiner—Patricia Bianco

(57) ABSTRACT

A confined air tube is intended to be placed into in-line communication with the transfer tubing of a blood processing system. The confined air tube provides an incremental volume of air, which keeps the transfer tubing from collapsing and sticking together during heat sterilization. After sterilization, the confined air tube accommodates conveyance of a blood component into an associated downstream transfer container. The confined air tube can also receive air vented from the transfer container, so that the blood component can undergo further processing or be stored in an air-depleted environment within the transfer container.

4 Claims, 10 Drawing Sheets

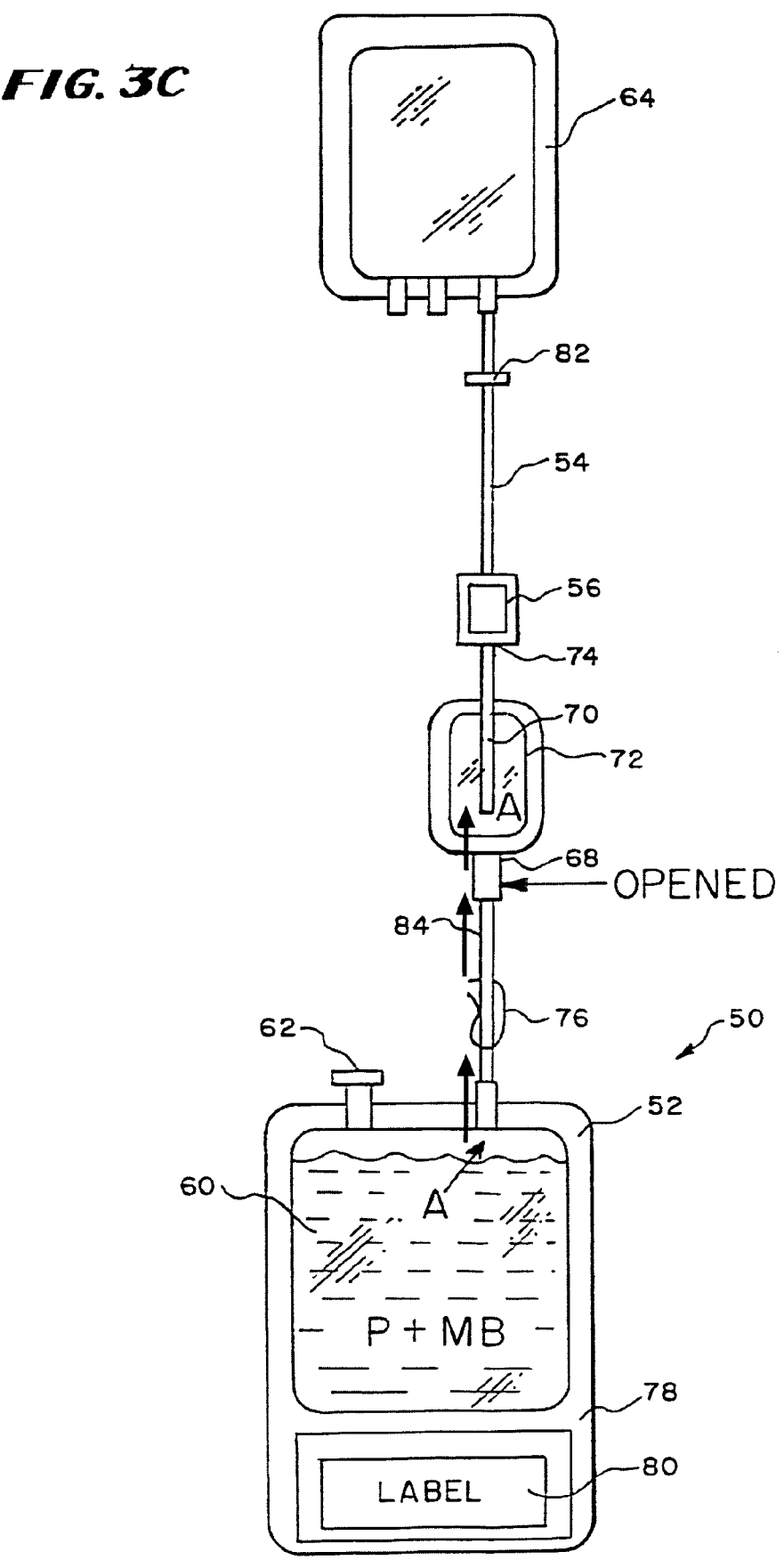

US 6,997,893 B2

CONFINED AIR TUBE AND METHODS FOR HANDLING AIR IN CLOSED BLOOD PROCESSING SYSTEMS

RELATED APPLICATIONS

This application is a continuation of co-pending U.S. patent application Ser. No. 09/902,313 filed 10 Jul. 2001 (now abandoned) which is a continuation of application Ser. No. 09/082,946 filed 21 May 1998 (now U.S. Pat. No. 6,267,745).

FIELD OF THE INVENTION

The invention generally relates to the blood collection systems and methods.

BACKGROUND OF THE INVENTION

FIG. 1 shows a representative prior art closed, multiple blood bag system 10. The system 10 includes a primary bag 12 and transfer bag 14, which are made, e.g., from medical grade plasticized polyvinyl chloride plastic. An outlet port 16 in the primary bag 12 communicates with an inlet port 18 in the transfer bag 14 through an integrally attached length of flexible transfer tubing 20, which is also made from medical grade plasticized polyvinyl chloride plastic. An inlet port 22 in the primary bag 12 communicates with a phlebotomy needle 24 through an integrally attached length of tubing 26. The primary bag 12 contains a suitable liquid anticoagulant 28. A frangible cannula 46 normally blocks liquid flow in the transfer tubing 20 from the primary bag 12 to the transfer bag 14. The system 10 therefore has a "wet" region (i.e., the primary bag 12 filled with liquid anticoagulant 28) and a "dry" (liquid free) region (i.e., the transfer bag 14 and the transfer tubing 20 downstream of the frangible cannula 46.

The system 10 is, before use, closed to communication with the atmosphere. The system 10 is heat sterilized in this closed condition, e.g., using steam. During heat sterilization, the walls of the dry transfer bag 14 and the dry transfer tubing 20 are prone to collapse and sticking together. To prevent this from occurring, conventional practice injects a volume of air or helium into the transfer bag 14 and tubing 20 prior to sterilization. This added step in manufacturing requires additional equipment and increases the labor cost. Furthermore, when the system is ultimately used to process blood, additional steps are often required to transfer or otherwise vent the residual air from the system 10. These air-handling steps can complicate and add to the cost of using the system 10.

SUMMARY OF THE INVENTION

The invention provides a confined air tube, which is intended to be placed into in-line communication with transfer tubing of a blood processing system. The air tube is confined in an air reservoir, into which the air tube extends a certain distance. The confined air tube provides an incremental volume of air, the magnitude of which depends upon the physical dimensions of the air tube. During heat sterilization, the incremental air volume keeps the transfer tubing from collapsing and sticking together. The presence of the confined air tube obviates the need to inject additional helium or air into the blood processing system during manufacture.

Another aspect of the invention incorporates the confined air tube in a blood processing system, to simplify blood processing techniques. In one mode, the confined air tube accommodates conveyance of a blood component into an associated transfer container. In an other mode, air can be vented from the transfer container into the air reservoir, so that the blood component can undergo further processing or be stored in an air-vented environment within the transfer container.

Other features and advantages of the invention will be pointed out in, or will be apparent from, the drawings, specification and claims that follow.

DESCRIPTION OF THE DRAWINGS

FIGS. 3B, 3C, and 3D are plan views of the system shown in FIG. 3A, as it is manipulated during use;

Figure 1:
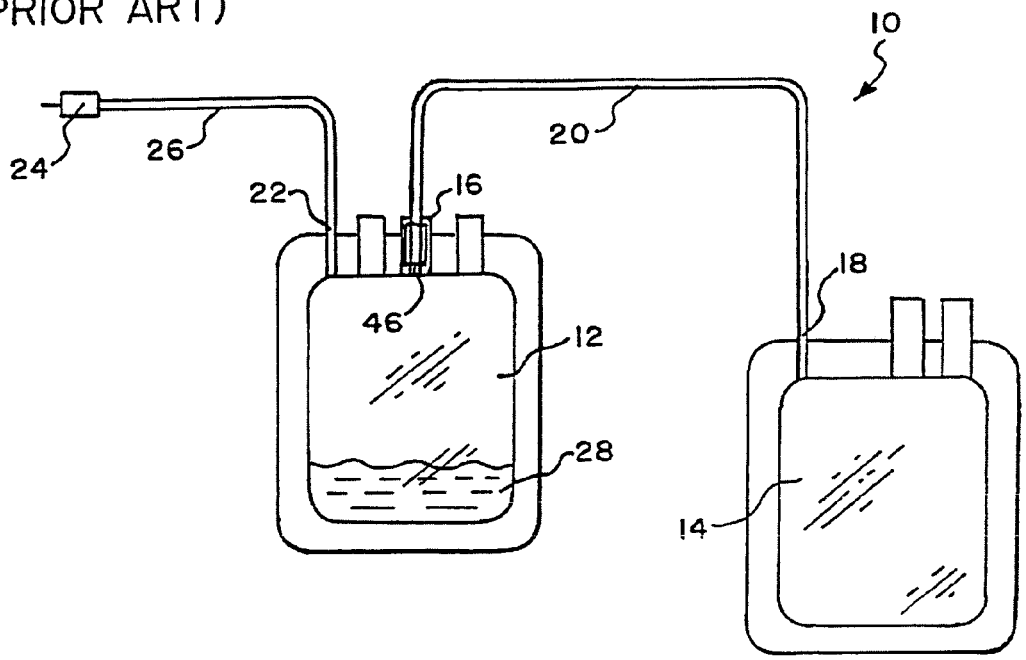
FIG. 1 is a plan view showing a representative prior art closed blood processing system.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

Figure 2B:
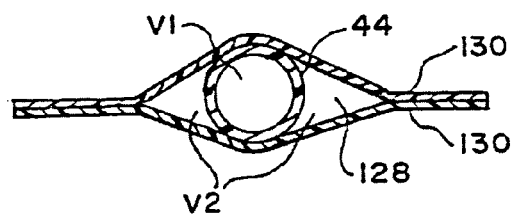
FIG. 2B is a top section view of the confined air tube taken generally along line 2B—2B in FIG. 2A.
Figure 2A:
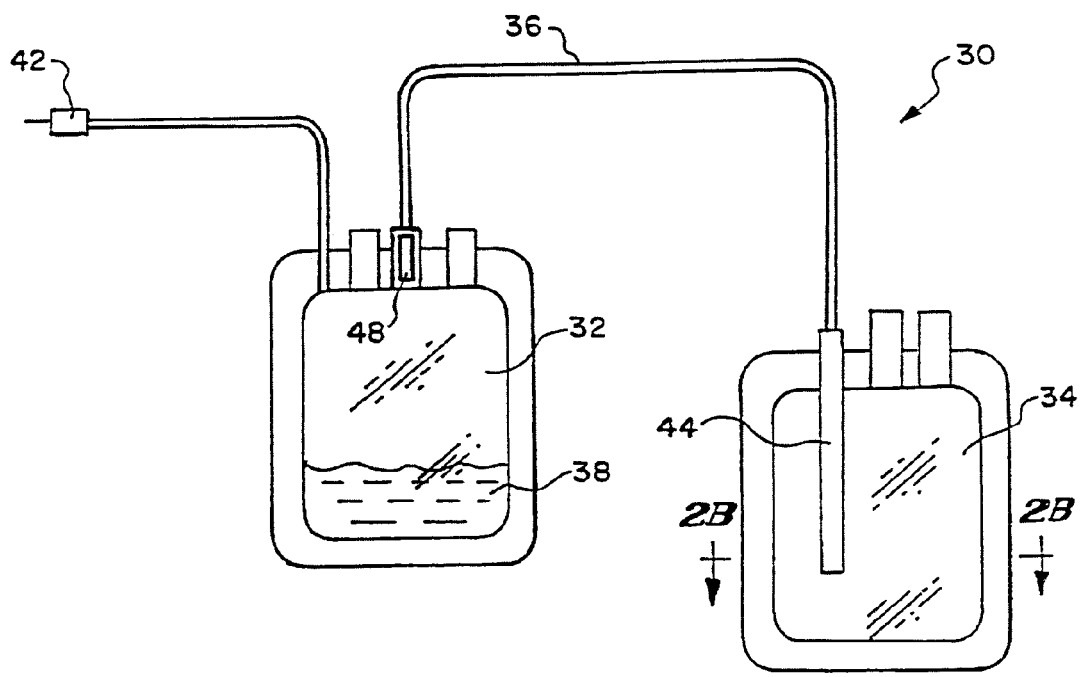
FIG. 2A is a plan view showing a closed blood processing system having a confined air tube, which embodies features of the invention.

FIG. 2A shows a closed, multiple blood bag system 30, which embodies features of the invention. Like the prior art system 10 shown in FIG. 1, the system includes a primary container 32 and transfer container 34 integrally attached by a length of transfer tubing 36. The primary container 32 carries a liquid anticoagulant 38 and tubing 40 terminating with a phlebotomy needle 42. The containers 32 and 34 and tubing 36 and 40 are made from plasticized polyvinyl chloride material, although other flexible medical grade plastic materials can be used.

A conventional frangible cannula 48 normally blocks liquid flow through the transfer tubing 36 from the primary container 32 to the transfer container 34. The transfer container 34 and tubing 36 are, before use, free of liquid. The system 30 is intended to be heat sterilized in the closed condition shown in FIG. 2A.

As FIGS. 2A and 2B show, the system 30 includes an air tube 44, which is confined within the dry transfer container 34. The air tube 44 communicates with the transfer tubing 36 and extends a certain distance into the dry transfer container 34. The air tube 44 contains a volume of residual air (shown as V1 in FIG. 2B). The space 128 created between the air tube 44 and the side walls 130 of the container 34, when in a normally empty condition, also contains a volume of residual air (shown as V2 in FIG. 2B). Together, the residual air volume of the air tube 44 and the residual air volume of the space 128 comprise an incremental volume of air ($V_i$=V1+V2) within the closed system 30. The presence of this incremental air volume Vi obviates the need to introduce added helium or air during manufacture to prevent collapse and sticking of the transfer container 34 and tubing 36.

The practitioner can empirically select an incremental air volume (Vi) sufficient to prevent collapse and sticking of the transfer container 34 and tubing 36 during heat sterilization. Generally stated, the magnitude of the residual air volume (V1) inside the air tube 44 is defined by the interior radius (R) and length (L) of the air tube 44, according to the following expression for the volume of a cylinder:

$$V1 = \Pi R^2 L$$

Also generally stated, the magnitude of the residual air volume (V2) is dependent principally upon the exterior radius and length of the air tube 44, about which the space 128 extends, as well as the surface area, flexibility and other physical properties of the container walls 130, which affect the geometry to which the walls 130 conform about the tube 44. As FIG. 2B shows, the flexible walls 130, when the container 34 is empty, define a space 128 about the air tube 44, which can be expected to be generally elliptical in cross section, with the magnitude of the major axis of the space 128 exceeding the magnitude of the outside diameter of the air tube 44. Due to this geometry, the residual air volume (V2) of the space 128 can be expected to be significantly larger than the residual air volume (V1) of the air tube 44.

For example, in a typical embodiment, the air tube 44 itself can provide a residual air volume (V1) of about 1.3 ml. In this arrangement, the space 128 created by the walls 130 conforming about the air tube 44 can provide a residual air volume (V2) of about 19 ml, for a total incremental air volume Vi of about 20 ml.

The presence of an air tube 44, confined within a liquid-free space 128 within a closed system, as shown in FIGS. 2A and 2B, can be implemented in many different ways. For example, FIG. 3A exemplifies another type of blood processing and storage system 50, which embodies features of the invention.

Figure 3A:
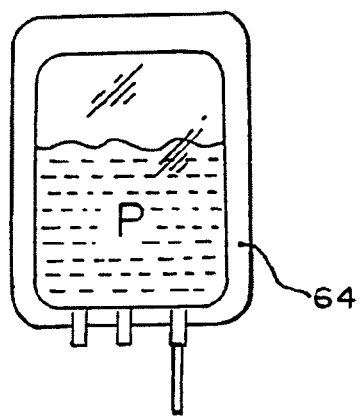
FIG. 3A is a plan view of another closed blood processing system for collecting and inactivating virus in plasma, the system having a confined air tube, which embodies features of the invention.
Figure 3A:
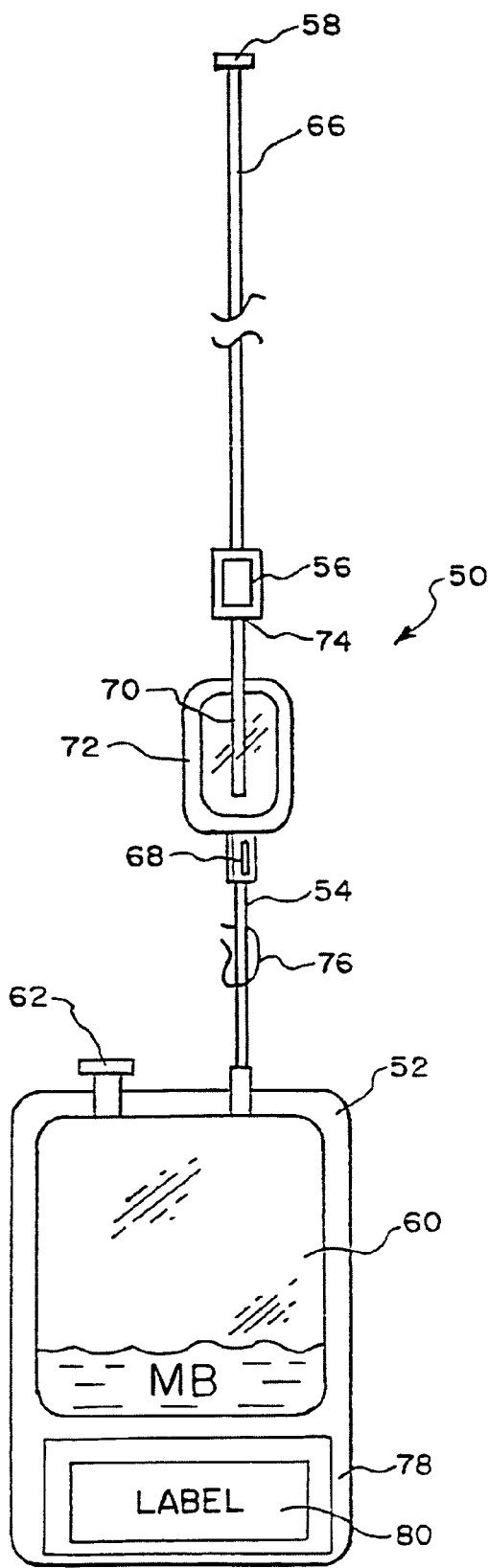

The system 50 shown in FIG. 3A is intended, during use, to assist in the removal of viral agents from plasma. The viral agents are either carried free within the plasma or are entrained on or within cellular matter (e.g., red blood cells, platelets, and leukocytes) that the plasma carries. In particular, the system 50 shown in FIG. 3A will be described in the context of reducing the presence of viral agents in single donor units of plasma, because it is particularly well suited for this purpose.

The system 50 includes a processing and storage container 52, which carries an integrally attached length of flexible transfer tubing 54. The container 52 is made of a material that is substantially transparent to the light energy applied during the photo activation process. The material for the container 52 is also adapted to withstand contemplated storage conditions for the plasma. In the illustrated embodiment, the container 52 is made of a plastic mixture of polyolefin materials, e.g., as made by Baxter Healthcare Corporation under the trademark PL-732® Plastic.

Figure 3B:
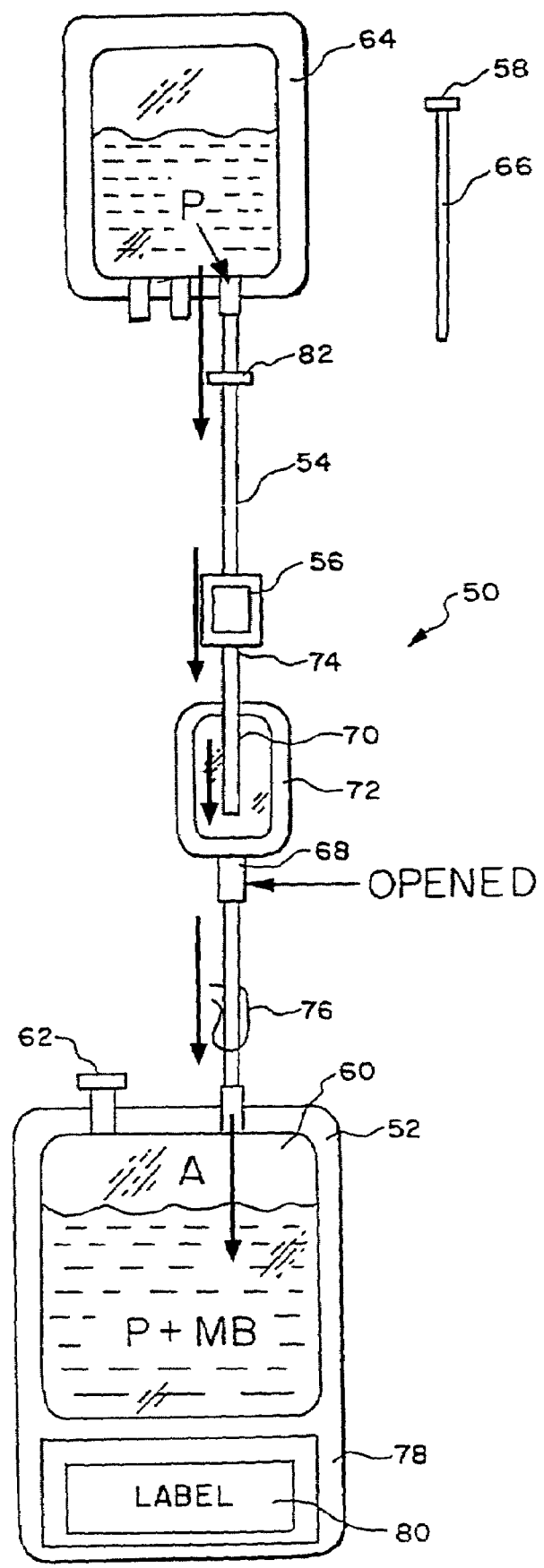

The processing and storage container 52 includes an interior chamber 60. The transfer tubing 54 communicates with the chamber 60 for conveying plasma into the chamber 60. The free end 66 of the tubing 54 in the system 50 is normally closed by a plug 58. During use, the free end 66 is coupled in a sterile fashion to a source of plasma P (shown as container 64 in FIG. 3B).

A normally sealed outlet port 62 also communicates with the chamber 60. The port 62 is opened when it is time to remove plasma from the chamber 60.

The chamber 60 holds a liquid solution containing a photo active material, e.g., methylene blue (thereby designed MB in FIG. 3A). The photo active solution MB mixes with the plasma P introduced into the chamber 60. The photo active material in the solution MB binds to extracellular viruses that plasma P introduced into the chamber 60 may carry. When exposed to light energy in a particular spectrum, the photo active material in the solution MB inactivates the nucleic acids of the bound viruses, rendering them nonviable.

The container 52 also includes a flap 78, which extends below the chamber 60. The flap 60 carries a printed label 80 having identifying indicia. The flap 78 keeps the label 80 away from the chamber 60, where it could block or impede the irradiating light.

A frangible cannula 68 normally closes liquid communication with the container 52 through the tubing 54. The transfer tubing 54 includes an integrally attached in-line filter 56 upstream of the frangible cannula 68. The filter 56 carries a filter medium that removes from plasma cellular matter that does actually or potentially entrain viral agents.

In the illustrated embodiment, the principal cellular species targeted by the filter 56 are leukocytes. The filter medium comprises one or more layers of a non-fibrous membrane, e.g. made from polycarbonate, nylon, acrylic copolymers, polysulfone, polyvinylidene fluoride, mixed cellulose esters, or cellulose ester, to remove leukocytes by exclusion. In the illustrated embodiment, the medium also includes a prefilter material, e.g., made from fibers of glass or polyester, which removes fibrin clots and other large size aggregates from the plasma. Further details of the in-line filter 56 can be found in copending U.S. patent application Ser. No. 08/742,572, entitled "Systems and Methods for Removing Viral Agents from Blood," filed Oct. 28, 1996.

The system 50 as described is, before use, a sealed, closed system having a "wet" region (i.e., the container 52) and a "dry" region (i.e., the transfer tubing 54 and the filter 56 upstream of the frangible cannula 68). The system 10 is heat sterilized in this condition.

To prevent the liquid-free region of the transfer tubing 54 (upstream of the frangible cannula 68) from collapsing and sticking together during heat sterilization, the system 50 includes a confined air tube 70. The air tube 70 is confined within an in-line air reservoir 72, which is located in the transfer tubing 54 between the filter 56 and the frangible cannula 68. The air tube 70 extends from the outlet 74 of the filter 56 a certain distance into the air reservoir 72. The air reservoir 72 comprises a peripherally sealed container made, e.g., of plasticized polyvinyl chloride material or another medical grade, heat sterilizable medical grade plastic material. Likewise, the air tube 70 is made from a heat sterilizable medical grade plastic material, like plasticized polyvinyl chloride.

The residual air volumes contained within the air tube 70 and the space created about it within the dry air reservoir 72, serve as the sources of an incremental volume of air ($V_i$) within the closed system 50. The presence of this incremental air volume ($V_i$) obviates the need to introduce added helium or air during manufacture to prevent collapse and sticking of the transfer tubing 54.

In a representative embodiment of the type shown in FIG. 3A, the air reservoir 72 measures about 80 mm by about 100 mm (between interior seals), for an interior volume of about 100 ml. The air tube 70 has an interior radius of about 9 mm and measures about 100 mm in length, providing a residual air volume (V1) of about 1.3 ml. A residual air volume (V2) of about 19 ml surrounds the air tube 70 within the reservoir 72, so that the total incremental air volume ($V_i$=V1+V2) is about 20 ml. The total volume of the transfer tubing 54 upstream of the frangible cannula 68 is about 12 ml. The total volume of the transfer tubing and the chamber 60 below the frangible cannula 68 is about 50 ml. The incremental air volume ($V_i$) of about 20 ml in this embodiment is sufficient to prevent collapse and sticking of the transfer tubing 54 during steam sterilization, without the injection of added helium or air. As will be described later, the volume of the air reservoir 72 is also sufficient to receive substantially all air vented from the chamber 60.

A normally opened, external roller clamp or C-clamp 76 of conventional construction is also present between the air reservoir 72 and processing and storage container 52, downstream of the frangible cannula 68, for reasons to be explained later.

In use (see FIG. 3B), the container 64 holding the plasma P is connected in a sterile fashion to the transfer tubing 54 near the plug 58. The source container 64 can, for example, hold fresh plasma or plasma that has been frozen and thawed. The plasma is harvested by conventional blood banking procedures.

Known sterile connection mechanisms (not shown) like that shown in Spencer U.S. Pat. No. 4,412,835 can be used for connecting the container 64 to the transfer tubing 54. These mechanisms form a molten seal between tubing ends, which, once cooled, forms a sterile weld 82.

Once the sterile connection is made, the plugged tubing end 66 is discarded. The source container 64 is suspended above the processing and storage container 52. The operator breaks the cannula 68 and leaves open the external C-clamp 76. The plasma P flows by gravity head pressure through the filter 56. The leukocyte-reduced plasma exits the filter 56 and drains into the chamber 60 of the container 52. The methylene blue photo active solution MB is mixed with the leukocyte-reduced plasma P within the container 52 by manual inversion.

As FIG. 3C shows, after mixing plasma P and photo active material solution MB within the container chamber 60, the container 52 is held upright and squeezed. Air A is vented from the container 52 into the reservoir 72. The venting of air A also displaces residual plasma P, out of the transfer tubing 54 between the filter 56 and the container 52 and into the reservoir 72. Viruses in the residual plasma P, having never entered the container chamber 60 have not been exposed to the photo active material solution MB and therefore should be removed before undertaking the desired photo activation process.

As air venting proceeds, an amount of the mixture of photo active material solution MB and plasma P will enter the section 84 of the transfer tubing 54 between the reservoir 72 and the container 52. The mixture exposes this section of the transfer tubing 54 with the photo active material solution MB, to assure that viruses still occupying this section of the tubing 54 are exposed during air venting with the photo active material solution MB. This assures that all viruses present in the container 52 and adjacent tubing section 84 are exposed to the material solution MB, to thereby assure the desired virucidal effect during subsequent exposure to light irradiation.

Figure 3D:
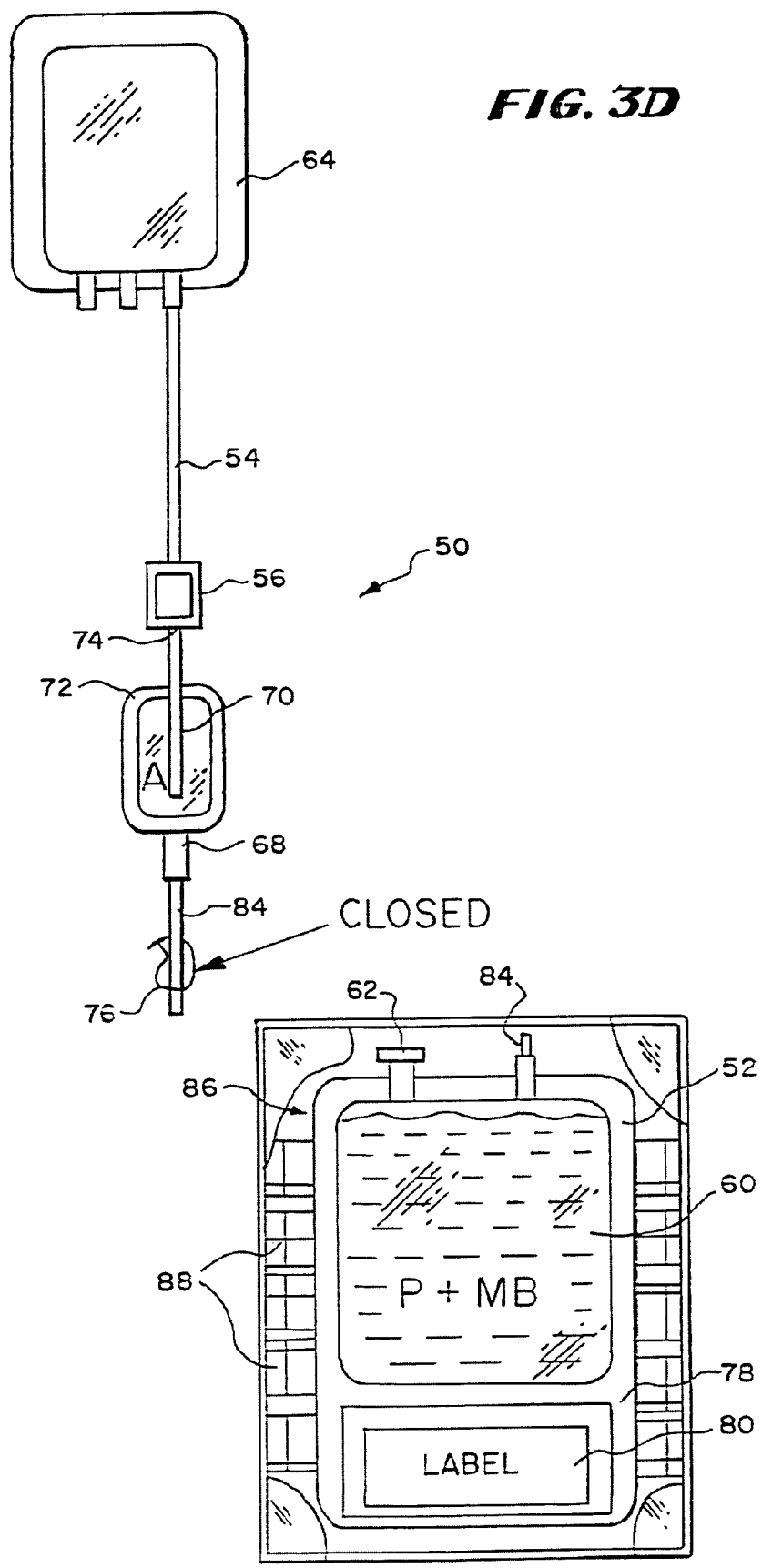

After air venting, the C-clamp 76 is closed to prevent air back-flow. The tubing section 84 is sealed closed using, for example, a dielectric tube sealer. As FIG. 3D shows, the remaining portion of the system 50 containing the filter 56 is removed and discarded. A remnant of the tubing 84 remains connected to the container 52.

The container 52 holding the methylene blue and leukocyte-reduced plasma, and carrying a remnant of the tubing section 84, is placed into a white light chamber 86. The chamber 86 comprises fluorescent lamps 88, which supply output in the visible range (400 to 700 nm) to both sides of the container 52. Alternatively, high pressure sodium lamps can be used. The light activates the methylene blue to release singlet oxygen, which inactivates viruses in the plasma.

After the illumination step, the leukocyte-reduced plasma is frozen within the container 52 at less than −30° C. for storage using conventional blood bank practices. The plasma within the container 52 is thawed when fractionation or transfusion is required.

Figure 4A:
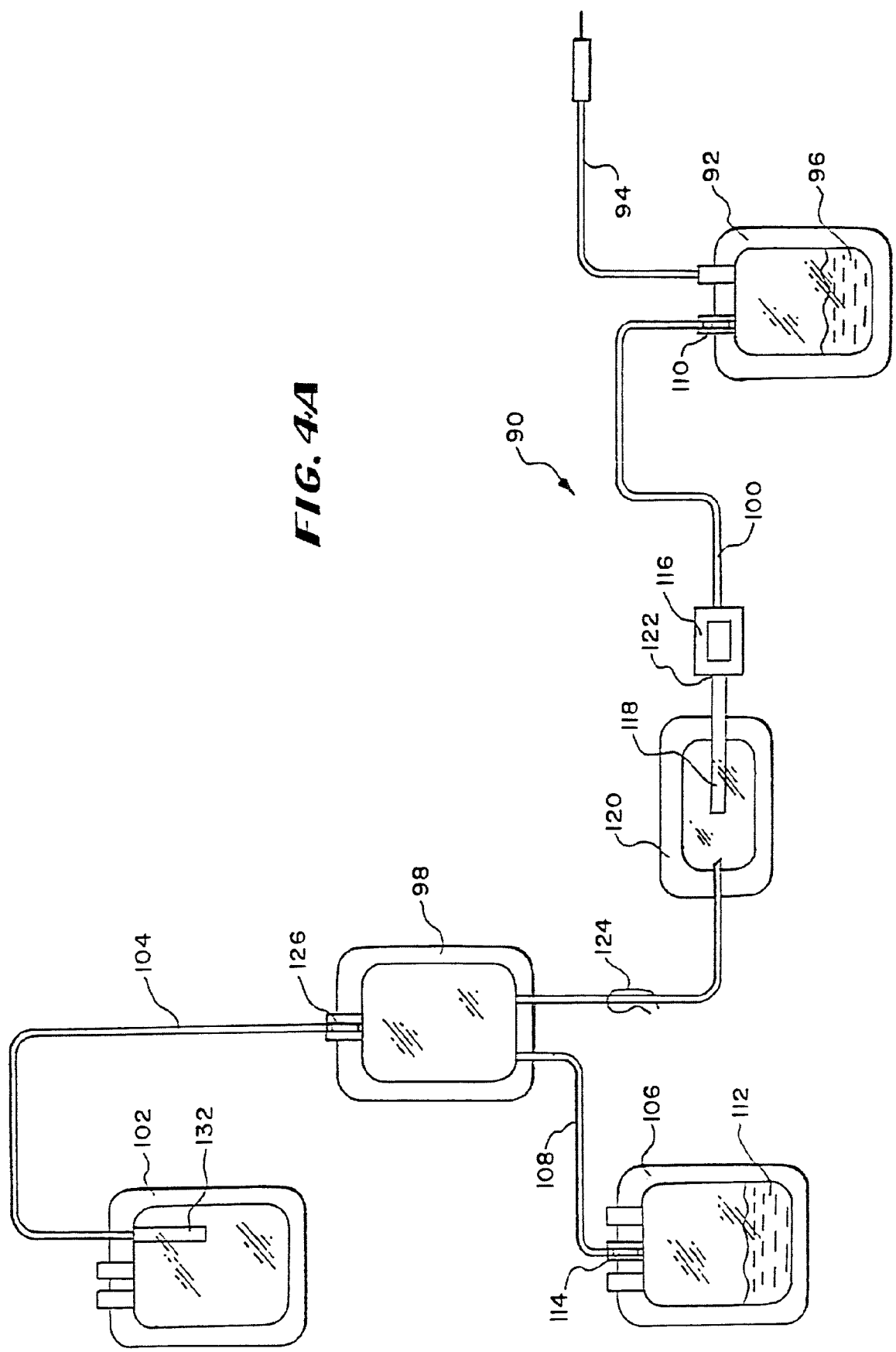
FIG. 4A is a plan view of another closed blood processing system for collecting plasma, red blood cells, and buffy coat from whole blood, the system having a confined air tube, which embodies features of the invention.

FIG. 4A shows an other type of blood collection system 90, which embodies features of the invention. In use, the system 90 processes whole blood into red blood cells, platelet-poor plasma, and buffy coat platelets.

The system 90 includes a primary container 92 with attached phlebotomy tubing 94. The primary container 92 holds a suitable anticoagulant solution 96. The primary container 92 communicates with a processing container 98 through integrally connected transfer tubing 100. The processing container 98 is coupled through a top port to a first transfer container 102, via integrally connected top transfer tubing 104. The processing container 98 is also coupled through a bottom port to a second transfer container 106, via integrally connected bottom transfer tubing 108.

The second transfer container 106 holds a storage solution 112. A frangible cannula 114 normally blocks liquid flow through the bottom transfer tubing 108. Another frangible cannula 126 normally blocks communication between the processing container 98 and the transfer container 102 through the top transfer tubing 104.

The transfer tubing 100 also includes a frangible cannula 110 in the outlet port of the primary container 92, which normally blocks liquid flow through the transfer tubing 100. Thus, the processing container 98 and the first transfer container 102 are, before use, free of liquid.

An in-line filter 116 is also carried by the transfer tubing. The filter 116 includes a conventional filtration medium to remove leukocytes from whole blood.

The system 90 in FIG. 4A is, before use, a sealed, closed system having "wet" (liquid-containing) regions (i.e., the primary container 92 and the second transfer container 106) and two "dry" (liquid free) regions. The first dry region comprises the transfer tubing 100 downstream of the frangible cannula 110, including the in-line filter 116, the processing container 98, as well as the transfer tubing 108 between the processing container 98 and the frangible cannula 114. The second dry region comprises the transfer tubing 104 and the first transfer container 102 downstream of the frangible cannula 126. The system 90 is heat sterilized in this condition.

To prevent the two liquid-free regions of the system 90 from collapsing and sticking together during heat sterilization, the system 90 includes first and second air tubes 118 and 132, which are confined, respectively, in an air reservoir 120 and the first transfer container 102.

Similar to the air tube 70 shown in FIG. 3A, the air tube 118 shown in FIG. 4A is confined within an in-line air reservoir 120. The air reservoir 120 is located in the transfer tubing 100 immediately downstream of the filter 116. The air tube 118 extends from the outlet 122 of the filter 116 a certain distance into the air reservoir 120. As previously described, both the air tube 118 and reservoir 120 can be made of plasticized polyvinyl chloride material or another medical grade, heat sterilizable medical grade plastic material. The first air tube 118 and the space created about it within the reservoir 120 provide incremental air for the first dry region.

Similar to the air tube 44 shown in FIG. 2A, the air tube 132 shown in FIG. 4A is confined within an transfer container 102. The air tube 132 extends a certain distance into the container 102. As previously described, both the air tube 132 and container 102 can be made of plasticized polyvinyl chloride material or another medical grade, heat sterilizable medical grade plastic material. The second air tube 132 and the space created about it within the container 102 provide incremental air for the second dry region.

The presence of these incremental air volumes obviates the need to introduce added helium or air during manufacture to prevent collapse and sticking of the transfer tubing 100, 104, and 108, the processing container 98, the transfer container 102, and the reservoir 120 itself.

A normally opened external roller clamp or C-clamp 124 of conventional construction is also present between the air reservoir 120 and processing container 98, for reasons to be explained later.

Figure 4B:
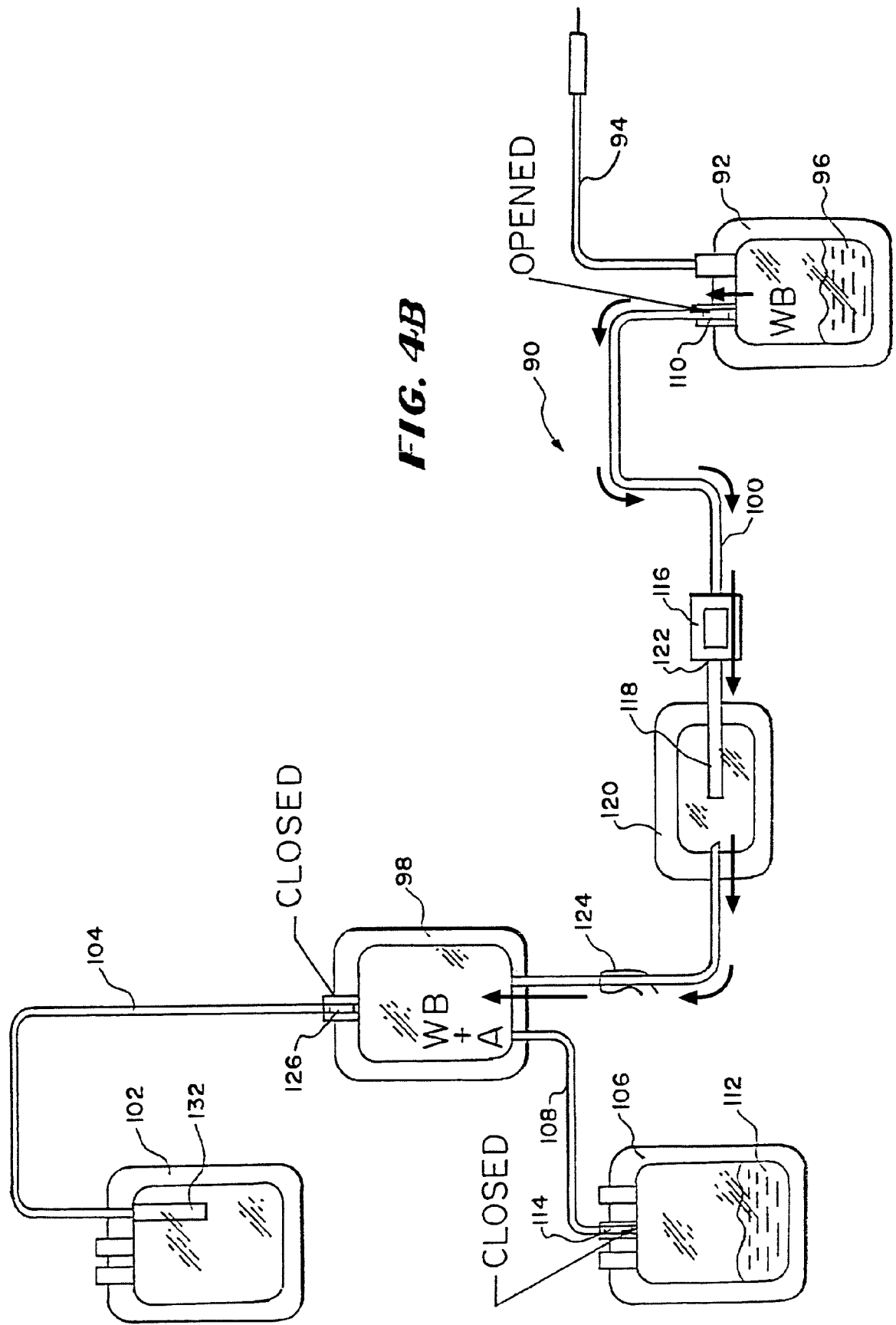
FIGS. 4B, 4C, 4D, and 4E are plan views of the system shown in FIG. 4A, as it is manipulated during use.

In use (see FIG. 4B), whole blood (WB) is collected in the primary container 92. The frangible cannula 110 is broken, and the C-clamp 124 is left opened. Whole blood is conveyed via the transfer tubing 100 through the in-line filter 116 and air reservoir 120 into the processing container 98. The filter 116 reduces the population of leukocytes in the whole blood before entry into the processing container 98.

Figure 4C:
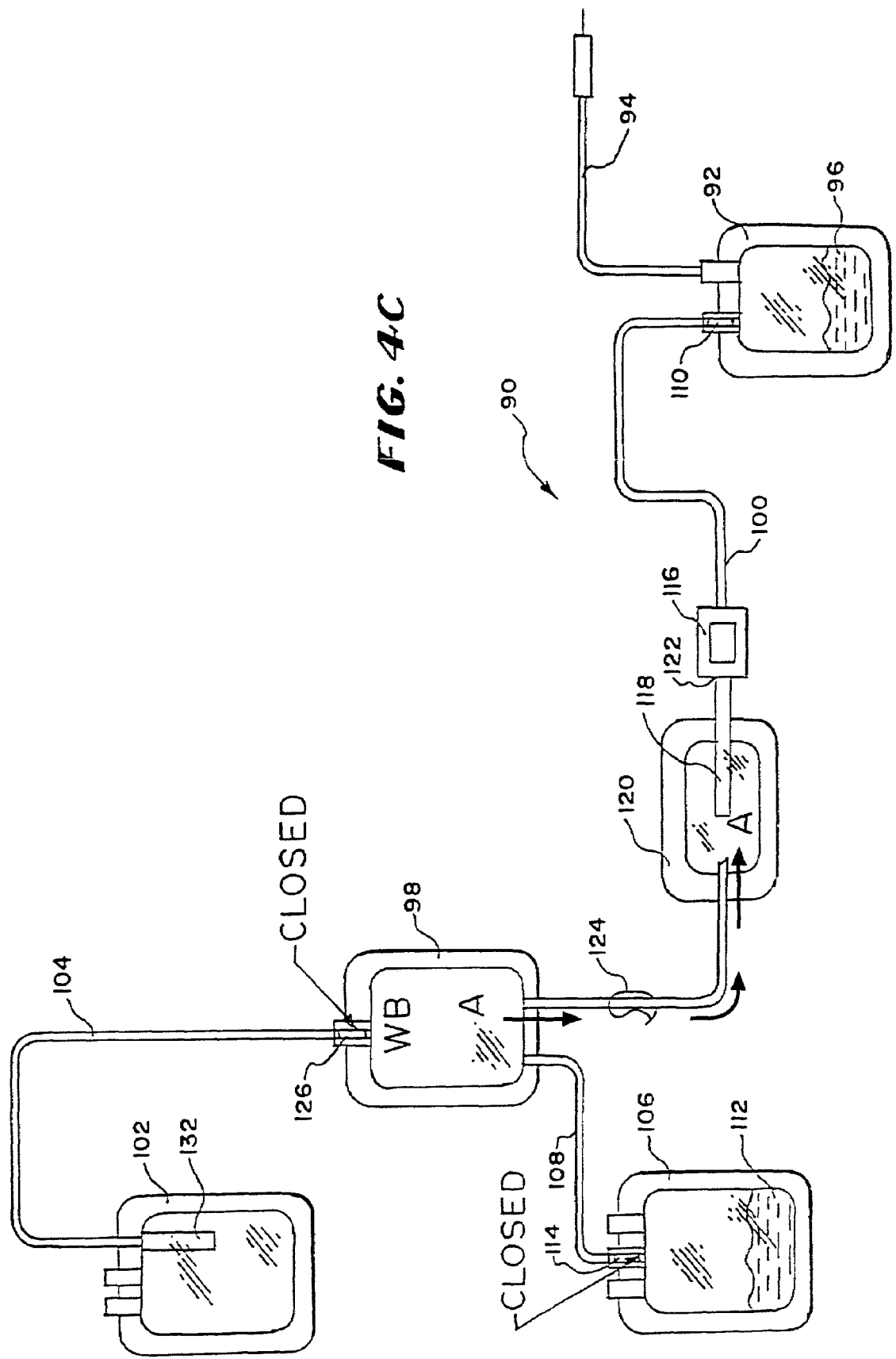

As FIG. 4C shows, once the processing container 98 is filled with filtered whole blood, air (A) is vented from the processing container 98 into the air reservoir 120. Although not shown in FIG. 4C, to vent the air A, the processing container 98 is turned upside down, so that the bottom transfer tubing 108 faces upward.

Figure 4D:
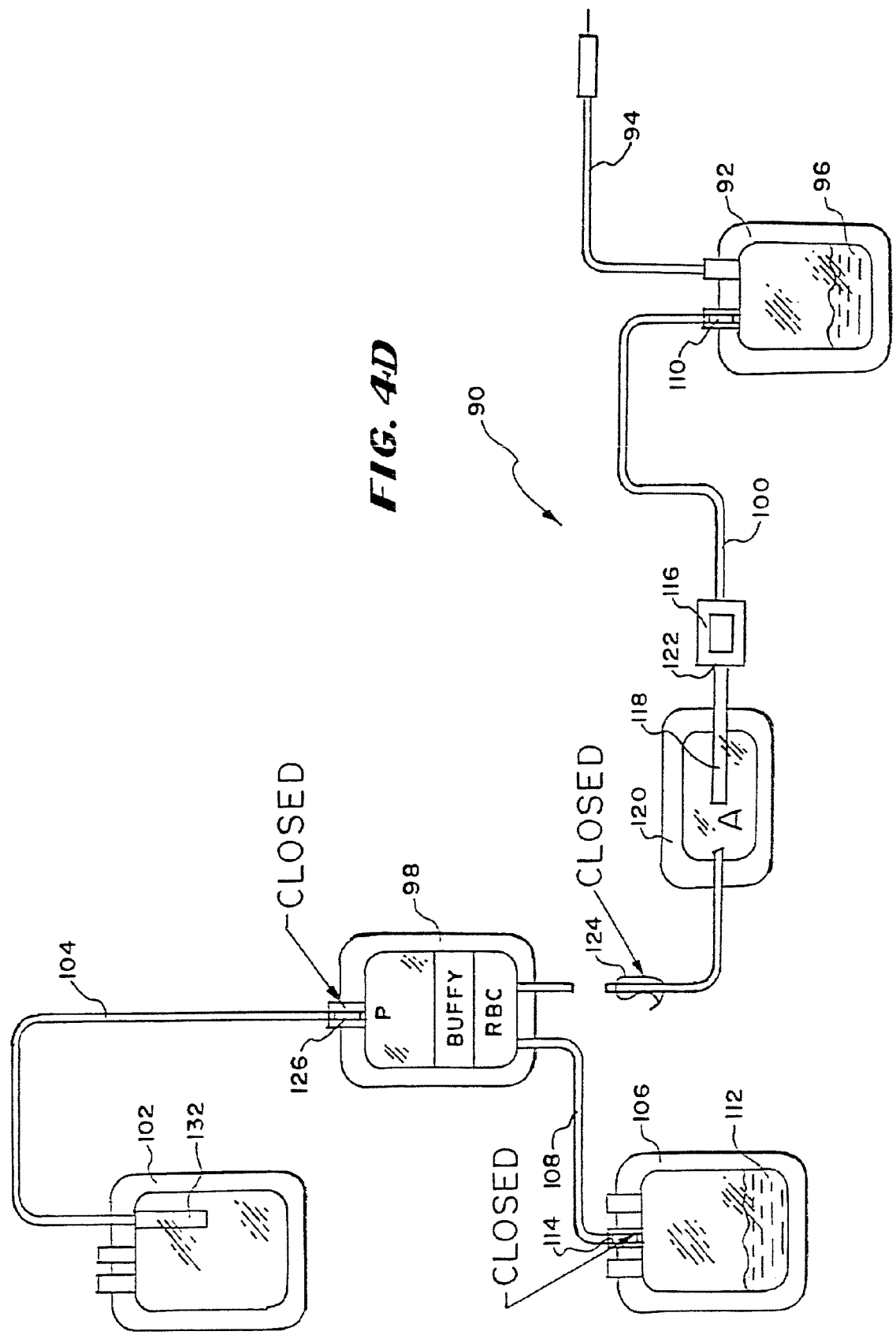

As FIG. 4D shows, once the air has been removed from the processing container 98, the C-clamp 124 is closed, to avoid air back flow. The transfer tubing 100 between the air reservoir 120 and processing container 98 is sealed, and primary container 92, the filter 116, and air reservoir 120 are separated as a unit from the rest of the system 90.

The processing container 98 is placed into a blood centrifuge, with the bottom of the container 98 oriented in the high-G field. As FIG. 4D shows, the whole blood separates into a layer of plasma (P), which collects near the top of the container 98; a layer of red blood cells (RBC), which collects near the bottom of the container 98; and a buffy coat layer (BUFFY) of platelets and remaining leukocytes, which collects in the container 98 between the layers of red blood cells and plasma.

Figure 4E:
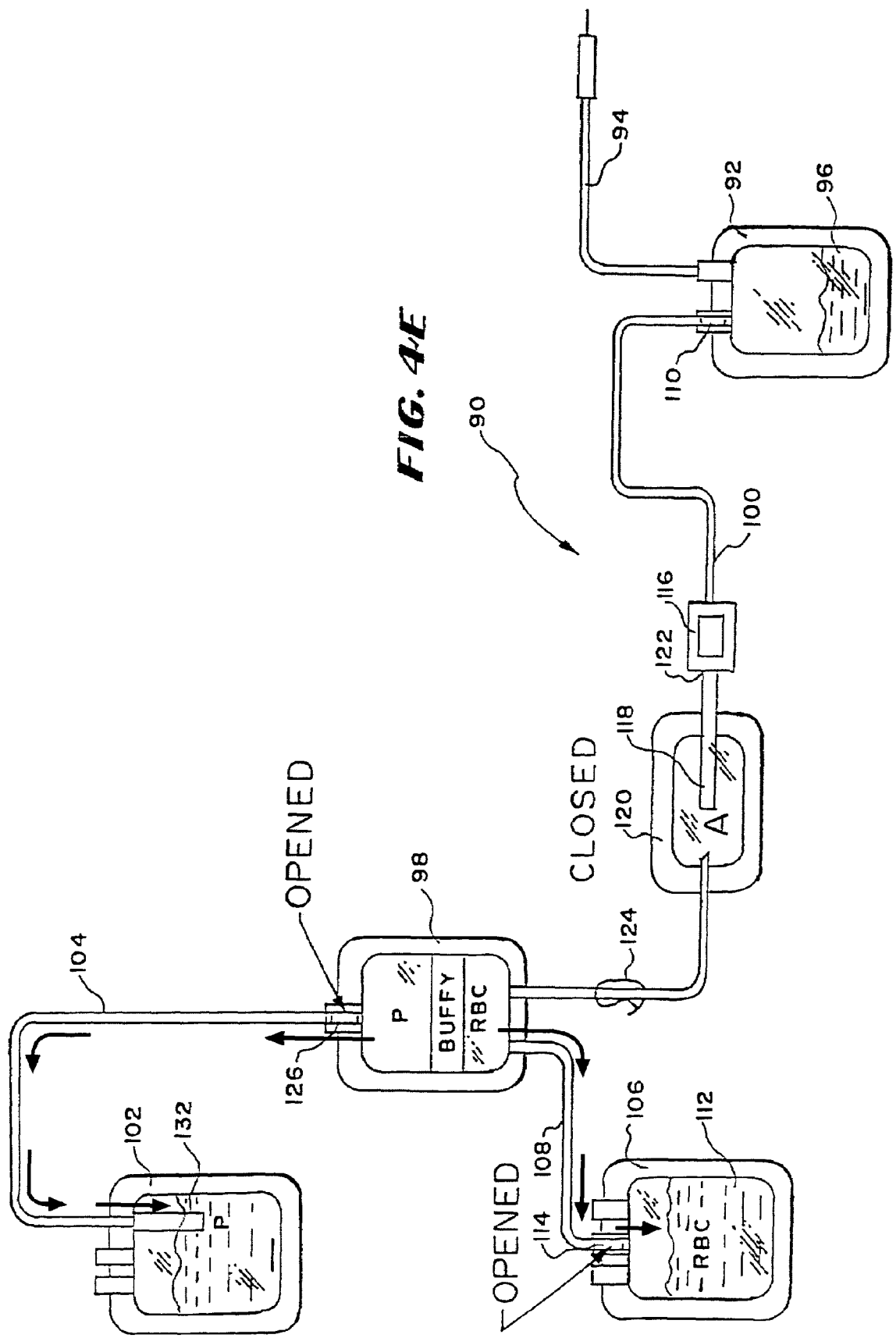

After centrifugation, the processing container 98 is placed into a press specially designed to accommodate containers with top and bottom ports, e.g., the Opti-Press® System sold by Baxter Healthcare Corporation. The frangible cannulas 114 and 126 are broken, and the press is actuated to squeezes the processing container 98. As FIG. 4E shows, plasma (P) exits through the top transfer tubing 104 and enters the top transfer container 102. Red blood cells (RBC) exit through the bottom transfer tubing 108 and enter the bottom transfer container 106, there mixing with the nutrient solution. The buffy coat layer remains in the processing container 98 for subsequent harvesting.

As demonstrated, the presence of a confined air tube within a closed multiple blood bag system eliminates the need to inject helium or air during manufacturing. When the air tube is confined inside a separate air reservoir, the air tube and reservoir together serve, during use of the associated system, as an in-line air receptor, which allows the user to shuttle air within the system in an uncomplicated, straightforward way during blood processing.

Features and advantages of the invention are set forth in the following claims.

We claim:

1. A heat sterilized blood processing system comprising a first container, flexible transfer tubing coupled in-line with the first container, the flexible transfer tubing including a peripheral wall made from flexible plastic material that, when subject to heat sterilization, is subject to collapsing and sticking together, a second container defining an air reservoir coupled in-line with the flexible transfer tubing, the second container including peripheral walls made from a flexible plastic material that, when subject to heat sterilization, are subject to collapsing and sticking together, and the flexible transfer tubing including an air tube extending a certain distance into the air reservoir and creating a space between the peripheral walls of the second container and the air tube, the air tube and the space being sized and configured to contain an incremental volume of air for the system so that the collapsing and sticking together of the peripheral wall of the flexible transfer tubing and the peripheral walls of the second container are prevented during heat sterilization.

2. A heat sterilized blood processing system according to claim 1 and further including an in-line filter carried by the flexible transfer tubing between the second container and the first container.

3. A heat sterilized blood processing system according to claim 1 further including a liquid carried by the first container during hear sterilization, and further including a frangible cannula normally blocking fluid flow through the flexible transfer tubing between the first and second container so that the second container and the flexible transfer tubing are, during heat sterilization, free of liquid.

4. A heat sterilized blood processing system according to claim 3 further including a phlebotomy needle coupled to the first container, and wherein the liquid includes an anticoagulant.

* * * * *